(12) United States Patent
Errico et al.

(10) Patent No.: US 11,259,845 B2
(45) Date of Patent: Mar. 1, 2022

(54) BONE ANCHOR APPARATUS AND METHOD OF USE THEREOF

(71) Applicant: K2M, Inc., Leesburg, VA (US)

(72) Inventors: Thomas J. Errico, New York, NY (US); Peter Newton, La Jolla, CA (US); Harry Shufflebarger, Jupiter, FL (US); Larry E. McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 16 days.

(21) Appl. No.: 16/498,214

(22) PCT Filed: Mar. 27, 2018

(86) PCT No.: PCT/US2018/024547
§ 371 (c)(1),
(2) Date: Sep. 26, 2019

(87) PCT Pub. No.: WO2018/183314
PCT Pub. Date: Oct. 4, 2018

(65) Prior Publication Data
US 2021/0077151 A1 Mar. 18, 2021

Related U.S. Application Data

(60) Provisional application No. 62/478,713, filed on Mar. 30, 2017.

(51) Int. Cl.
*A61B 17/70* (2006.01)
*A61B 17/88* (2006.01)
*A61B 17/56* (2006.01)

(52) U.S. Cl.
CPC ...... *A61B 17/7032* (2013.01); *A61B 17/8888* (2013.01); *A61B 2017/564* (2013.01)

(58) Field of Classification Search
CPC ............ A61B 17/7032; A61B 17/8888; A61B 17/686; A61B 17/861; A61B 17/8605;
(Continued)

(56) References Cited

U.S. PATENT DOCUMENTS 5,382,248 A 1/1995 Jacobson et al.
5,487,744 A 1/1996 Howland
(Continued)

OTHER PUBLICATIONS

International Search Report for PCT/US2018/24547, dated May 11, 2018, 2 pages.
(Continued)

*Primary Examiner* — Pedro Philogene
(74) *Attorney, Agent, or Firm* — Lerner, David, Littenberg, Krumholz & Mentlik, LLP (57) ABSTRACT

A bone fixation apparatus includes an insert and a bone anchor. The insert has open ends defining a lumen. A first thread is disposed on an outer surface of the insert and a second thread is disposed in the lumen. The insert is configured for threadably engaging bone. A driving tool is releasably attachable to the insert. The bone fixation apparatus also includes a bone anchor with a bone screw member and a housing. The bone screw member extends from the housing and has a third thread along a shank of the bone screw member. The third thread of the shank is engageable with the second thread of the lumen such that the bone anchor is coupled to the insert.

15 Claims, 10 Drawing Sheets

(58) Field of Classification Search
CPC .............. A61B 17/864; A61B 17/8625; A61B 2017/564
USPC ................................. 606/300–328, 246–289
See application file for complete search history.

(56) References Cited

U.S. PATENT DOCUMENTS

| | | | |
|---|---|---|---|
| 5,725,528 A | 3/1998 | Errico et al. | |
| 5,735,851 A | 4/1998 | Errico et al. | |
| 5,800,435 A | 9/1998 | Errico et al. | |
| 6,004,322 A | 12/1999 | Bernstein | |
| 6,050,997 A | 4/2000 | Mullane | |
| 6,146,383 A | 11/2000 | Studer et al. | |
| 6,482,207 B1 | 11/2002 | Errico | |
| 6,623,485 B2 | 9/2003 | Doubler et al. | |
| 6,669,697 B1 | 12/2003 | Pisharodi | |
| 6,887,242 B2 | 5/2005 | Doubler et al. | |
| 7,186,255 B2 | 3/2007 | Baynham et al. | |
| 7,314,467 B2 | 1/2008 | Howland | |
| 7,722,645 B2 | 5/2010 | Bryan | |
| 7,766,943 B1 | 8/2010 | Fallin et al. | |
| 8,007,518 B2 | 8/2011 | Winslow et al. | |
| 8,012,181 B2 | 9/2011 | Winslow et al. | |
| 8,016,861 B2 | 9/2011 | Mitchell et al. | |
| 8,048,115 B2 | 11/2011 | Winslow et al. | |
| 8,048,126 B2 | 11/2011 | Altarac et al. | |
| 8,057,515 B2 | 11/2011 | Flynn et al. | |
| 8,075,603 B2 | 12/2011 | Hammill, Sr. et al. | |
| 8,083,772 B2 | 12/2011 | Winslow et al. | |
| 8,083,775 B2 | 12/2011 | Winslow et al. | |
| 8,083,777 B2 | 12/2011 | Butters et al. | |
| 8,092,501 B2 | 1/2012 | Mitchell et al. | |
| 8,097,024 B2 | 1/2012 | Winslow et al. | |
| 8,114,134 B2 | 2/2012 | Winslow et al. | |
| 8,128,670 B2 * | 3/2012 | Ralph ................ | A61B 17/8038 606/313 |
| 8,137,384 B2 | 3/2012 | Heiges et al. | |
| 8,192,468 B2 | 6/2012 | Biedermann et al. | |
| 8,192,470 B2 | 6/2012 | Biedermann et al. | |
| 8,197,518 B2 | 6/2012 | Hammill, Sr. et al. | |
| 8,211,155 B2 | 7/2012 | Winslow et al. | |
| 8,257,397 B2 | 9/2012 | Winslow et al. | |
| 8,333,792 B2 | 12/2012 | Winslow et al. | |
| 8,337,530 B2 | 12/2012 | Hestad et al. | |
| 8,337,536 B2 | 12/2012 | Mitchell et al. | |
| 8,430,916 B1 | 4/2013 | Winslow et al. | |
| 8,506,609 B2 | 8/2013 | Biedermann et al. | |
| 8,518,085 B2 | 8/2013 | Winslow et al. | |
| 8,636,781 B2 | 1/2014 | Biedermann et al. | |
| 8,636,782 B2 | 1/2014 | Biedermann et al. | |
| 8,663,290 B2 | 3/2014 | Doubler et al. | |
| 8,663,291 B2 | 3/2014 | Doubler et al. | |
| 8,881,358 B2 | 11/2014 | Biedermann et al. | |
| 8,900,270 B2 | 12/2014 | Fauth et al. | |
| 8,926,671 B2 | 1/2015 | Biedermann et al. | |
| 8,961,568 B2 | 2/2015 | McKinley et al. | |
| 8,979,904 B2 | 3/2015 | Jackson et al. | |
| 8,986,349 B1 | 3/2015 | German et al. | |
| 8,992,579 B1 | 3/2015 | Gustine et al. | |
| 8,998,958 B2 | 4/2015 | Dauster et al. | |
| 9,017,390 B2 | 4/2015 | Biedermann et al. | |
| 9,044,273 B2 | 6/2015 | Richelsoph et al. | |
| 9,060,814 B2 | 6/2015 | Doubler et al. | |
| 9,066,759 B2 | 6/2015 | Biedermann et al. | |
| 9,119,674 B2 | 9/2015 | Matthis et al. | |
| 9,131,971 B2 | 9/2015 | Biedermann et al. | |
| 9,173,684 B2 | 11/2015 | Biedermann et al. | |
| 9,186,187 B2 | 11/2015 | Mishra | |
| 9,198,694 B2 | 12/2015 | Mishra et al. | |
| 9,247,965 B2 | 2/2016 | Biedermann et al. | |
| 9,254,150 B2 | 2/2016 | Biedermann et al. | |
| 9,277,938 B2 | 3/2016 | Biedermann et al. | |
| 9,277,941 B2 | 3/2016 | Biedermann et al. | |
| 9,277,942 B2 | 3/2016 | Biedermann et al. | |
| 9,333,016 B2 | 5/2016 | Biedermann et al. | |
| 9,339,304 B2 | 5/2016 | Biedermann et al. | |
| 9,358,047 B2 | 6/2016 | Mishra et al. | |
| 9,364,266 B2 | 6/2016 | Biedermann et al. | |
| 9,393,049 B2 | 7/2016 | Jones et al. | |
| 9,439,680 B2 | 9/2016 | Biedermann et al. | |
| 9,451,990 B2 | 9/2016 | Fauth et al. | |
| 9,452,006 B2 | 9/2016 | Biedermann et al. | |
| 9,486,246 B2 | 11/2016 | Biedermann et al. | |
| 9,492,204 B2 | 11/2016 | Biedermann et al. | |
| 9,579,125 B2 | 2/2017 | Raju et al. | |
| 9,603,635 B2 | 3/2017 | Leff et al. | |
| 9,615,858 B2 | 4/2017 | Doubler et al. | |
| 9,649,142 B2 | 5/2017 | Doubler et al. | |
| 9,693,808 B2 | 7/2017 | Fauth et al. | |
| 9,707,013 B2 | 7/2017 | Rezach et al. | |
| 9,820,780 B2 | 11/2017 | Duncan et al. | |
| 9,883,892 B2 | 2/2018 | Jackson et al. | |
| 9,895,170 B2 | 2/2018 | Biedermann et al. | |
| 9,895,171 B2 | 2/2018 | Webb | |
| 9,907,574 B2 | 3/2018 | Jackson et al. | |
| 9,918,745 B2 | 3/2018 | Jackson et al. | |
| 9,936,983 B2 | 4/2018 | Mesiwala et al. | |
| 9,980,753 B2 | 5/2018 | Jackson et al. | |
| 2002/0151977 A1 * | 10/2002 | Paes ................ | A61F 2/446 623/17.11 |
| 2003/0060823 A1 | 3/2003 | Bryan | |
| 2004/0210227 A1 * | 10/2004 | Trail .................... | A61B 17/863 606/916 |
| 2008/0039846 A1 | 2/2008 | Lee et al. | |
| 2010/0057135 A1 | 3/2010 | Heiges et al. | |
| 2011/0118783 A1 | 5/2011 | Winslow et al. | |
| 2011/0307018 A1 | 12/2011 | Zucherman et al. | |
| 2012/0041490 A1 | 2/2012 | Jacob et al. | |
| 2012/0143262 A1 | 6/2012 | Jensen et al. | |
| 2012/0150233 A1 | 6/2012 | Heiges et al. | |
| 2012/0259372 A1 * | 10/2012 | Glazer ................. | A61B 17/686 606/301 |
| 2012/0265258 A1 | 10/2012 | Garvey | |
| 2015/0196338 A1 | 7/2015 | Biedermann et al. | |
| 2016/0030086 A1 | 2/2016 | Mishra | |
| 2016/0030090 A1 | 2/2016 | Webb | |
| 2016/0100870 A1 | 4/2016 | Lavigne et al. | |
| 2016/0106475 A1 * | 4/2016 | Potash ............... | A61B 17/7086 606/266 |
| 2016/0220277 A1 | 8/2016 | Rezach et al. | |
| 2017/0020574 A1 | 1/2017 | Biedermann et al. | |
| 2017/0049482 A1 | 2/2017 | Campbell et al. | |
| 2017/0049484 A1 | 2/2017 | Leff et al. | |
| 2017/0065306 A1 | 3/2017 | Fauth et al. | |
| 2017/0112542 A1 | 4/2017 | Biedermann et al. | |
| 2017/0172630 A1 | 6/2017 | Biedermann et al. | |
| 2017/0224386 A1 | 8/2017 | Leff et al. | |
| 2017/0245898 A1 | 8/2017 | May et al. | |
| 2017/0333085 A1 | 11/2017 | Jackson et al. | |
| 2018/0014858 A1 | 1/2018 | Biester et al. | |
| 2018/0014862 A1 | 1/2018 | Raina et al. | |
| 2018/0014863 A1 | 1/2018 | Biester et al. | |
| 2018/0036039 A1 | 2/2018 | Biedermann et al. | |
| 2018/0055545 A1 | 3/2018 | Biedermann et al. | |
| 2018/0092679 A1 | 4/2018 | Toon et al. | |
| 2018/0110548 A1 | 4/2018 | May et al. | |

OTHER PUBLICATIONS

Extended European Search Report for Application No. EP18775534.3, dated Jan. 11, 2021, pp. 1-3.

* cited by examiner

BONE ANCHOR APPARATUS AND METHOD OF USE THEREOF

CROSS-REFERENCE TO RELATED APPLICATIONS

The present application is a national phase entry under 35 U.S.C. § 371 of International Application No. PCT/US2018/024547, filed on Mar. 27, 2018, which claims priority to, and the benefit of, U.S. Provisional Patent Application Ser. No. 62/478,713, filed Mar. 30, 2017, the entireties of which are hereby incorporated by reference.

TECHNICAL FIELD

The present disclosure relates to spinal implants and, more particularly, to a bone anchor apparatus and a method of using the bone anchor apparatus.

BACKGROUND

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

The mechanical hardware used to immobilize the spinal column typically involves a series of bone screws and metal rods or plates. When the spine surgery is performed, it is common practice to place bone screws into the vertebral bodies and then connect a metal rod between the screws, thus creating a rigid structure between adjacent vertebral bodies. In some cases, these devices may be permanently implanted in the patient. In other cases, the devices may be implanted only as a temporary means of stabilizing or fixing the bones or bone fragments, with subsequent removal when no longer needed.

When using screws, the surgeon directs the screw into the vertebral body. Because different patients have different anatomies, there exists the potential for part of the vertebral body to be breached. A breach occurs when the screw protrudes through the bone on either the lateral or medial side. Often, if there is a lateral breach, the surgeon leaves the screw in place. If the breach occurs medially into the spinal canal, the spinal nerves can rub against the threads causing the patient pain and possibly requiring a revision surgery. Typically, when the surgeon recognizes the breach, he uses an instrument to displace the nerves to protect them from damage, removes the original screw and redirects it. Redirection removes more bone and can compromise fixation of the screw or completely damage the vertebral body rendering it unusable as a point of device fixation.

SUMMARY

According to one embodiment of the present disclosure a bone fixation apparatus includes an insert having an open proximal end and an open distal end defining a lumen therethrough. The open proximal end has a geometric pattern for mating with a driving tool. A first helical thread is disposed on an outer surface of the insert and is configured to engage bone. A second helical thread is disposed in the lumen of the insert. The bone fixation apparatus also includes a bone anchor having a bone screw member and a housing. The bone screw member includes a spherical head and a shank extending therefrom. The shank has a third helical thread on an outer surface thereof and the spherical head is movably retained in a cavity of the housing. The first helical thread is engageable with the third helical thread such that the bone anchor is coupled to the insert.

In embodiments, the first and third helical threads may be reversed from the second helical thread.

In embodiments, the open proximal end may include alternating lobes and recesses defining a hexolobular geometric configuration.

In embodiments, the first helical thread may be configured to engage osseous tissue in a pedicle of a vertebra.

In embodiments, the lumen of the insert may slidably receive a portion of the driving tool.

In embodiments, a major diameter of the first helical thread may be between about 10 mm and about 12 mm. The major diameter of the first helical thread may taper along a length of the insert. The major diameter may taper from a proximal end of the insert towards the distal end of the insert at a ratio of about 1.4 to about 1.7. An angle of the taper may be between about 18 degrees and about 56 degrees.

According to an embodiment of the present disclosure, a method of inserting a bone fixation apparatus is disclosed. The method includes attaching an insert to a driving tool and positioning a distal portion of the driving tool proximate a target location on bone such that the insert is proximate the opening. The method also includes securing the insert in bone by rotating the driving tool such that a first thread of the insert rotatably engages bone in the opening. The method also includes removing the driving tool from the insert and coupling a bone anchor to the insert wherein the bone anchor includes a housing and a screw member with a threaded shank engageable with a second thread in a lumen of the insert.

In embodiments, the method may include creating an opening in the vertebra at the target location.

In embodiments, the method may include preparing a preexisting opening at the target location to receive the insert therein.

In embodiments, the method may include the opening or the preexisting opening disposed on a pedicle of the vertebra.

In embodiments, the method may include the bone anchor having a modular housing.

BRIEF DESCRIPTION OF THE DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure, wherein.

DETAILED DESCRIPTION OF THE EMBODIMENTS

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably and should be understood as referring to the portion of a structure that is closer to a clinician during proper use. The term "clinician" refers to a doctor (e.g., a surgeon), a nurse, or any other care provider, and may include support personnel. The terms "distal" and "leading" may also be employed interchangeably and should be understood as referring to the portion of a structure that is farther from the clinician during proper use. In addition, the term "cephalad" is used in this application to indicate a direction toward a patient's head, whereas the term "caudad" indicates a direction toward the patient's feet. Further still, the term "medial" indicates a direction toward the middle of the body of the patient, while the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Figure 1A:
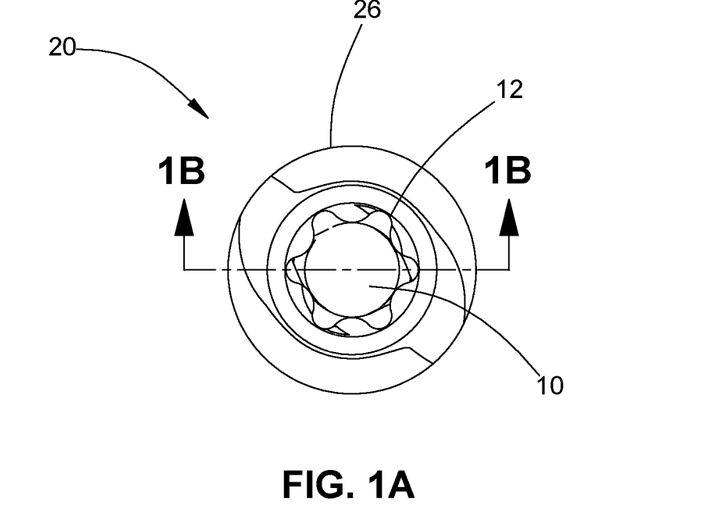
FIG. 1A is a top plan view of an insert.
Figure 1B:
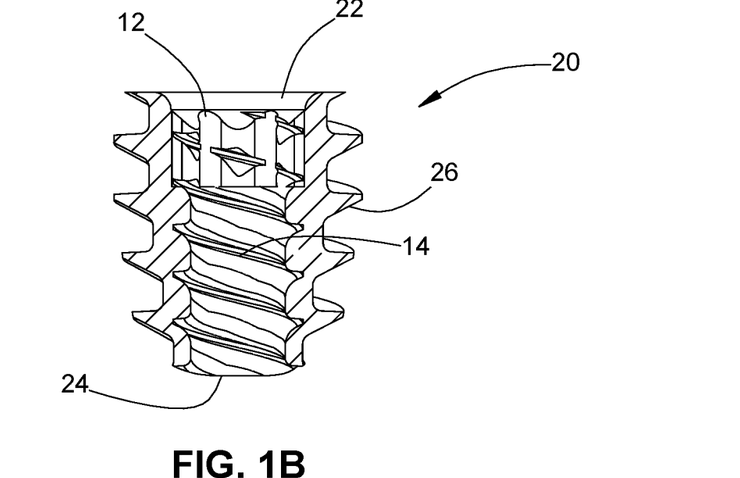
FIG. 1B is a side cross-sectional view of the insert of FIG. 1A taken along section line 1B-1B of FIG. 1A.
Figure 1C:
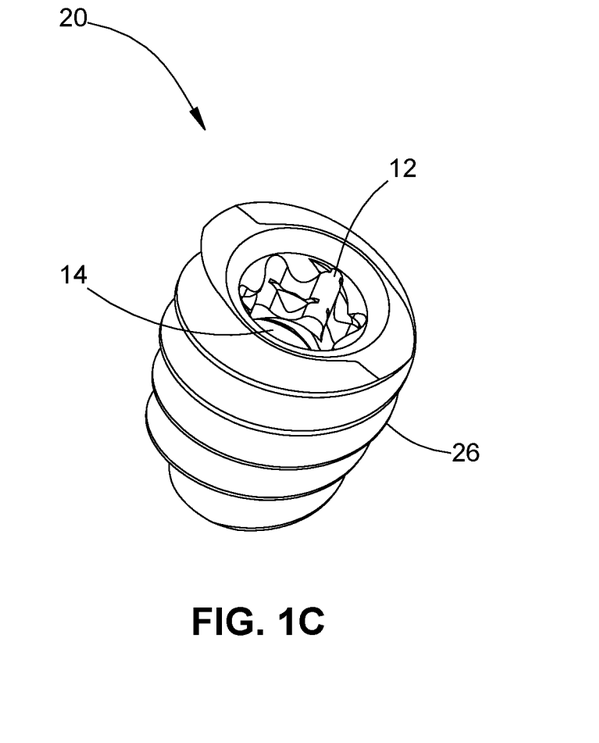
FIG. 1C is a top perspective view of the insert of FIG. 1A.
Figure 2A:
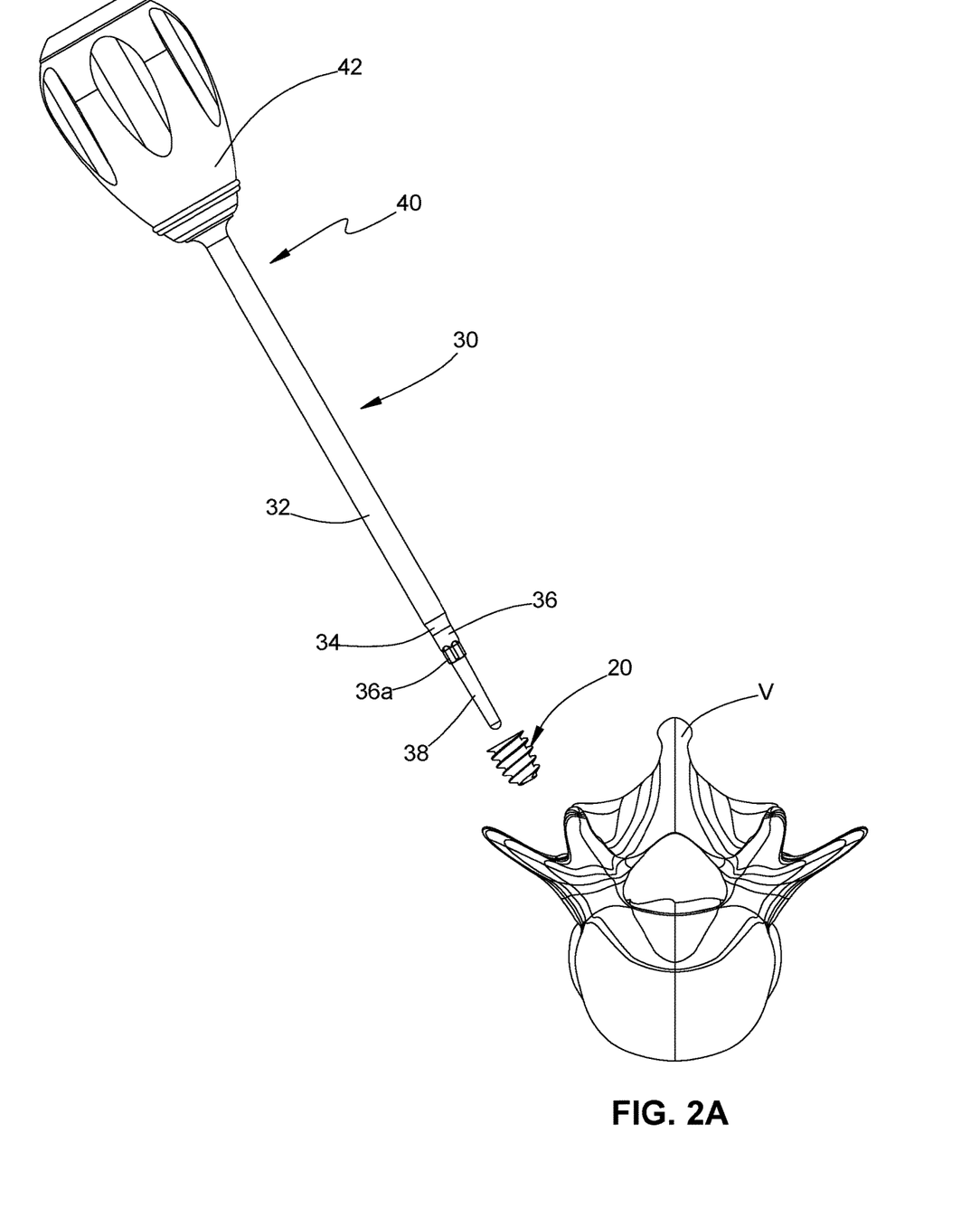
FIG. 2A is a perspective view of the insert of FIG. 1A and an insertion instrument prior to positioning the insert into a vertebra.

With initial reference to FIGS. 1A-1C, an insert 20 according to an embodiment of the present disclosure is illustrated. Insert 20 has an open proximal end 22 and an open distal end 24 defining a passage or lumen 10 therethrough. The lumen 10 has an engagement portion 12 located in a proximal region of the lumen 10. The engagement portion 12 of the lumen 10 has a geometric configuration for complementary engagement with a driving or insertion tool 40 (FIG. 2A). In the illustrated example of FIG. 1C, the engagement portion 12 has alternating lobes and recesses defining a generally hexolobular configuration. It is contemplated that the illustrated hexolobular configuration may be replaced by another geometric configuration (e.g., star, square, etc.) that complements an engagement portion of the insertion tool 40 thereby providing positive engagement between insertion tool 40 and insert 20.

The lumen 10 also includes an internal or first thread 14 that extends distally from proximal end 22 to a distal end of the lumen 10 that corresponds to the open distal end 24 of the insert 20. In one embodiment, the first thread 14 originates at the proximal end 22 and terminates at the open distal end 24. The internal thread 14 is a helical thread and may be a right-hand thread (i.e., clockwise to tighten) or a left-hand thread (i.e., counter-clockwise to tighten). Similarly, an outer surface of insert 20 has an external or second thread 26 disposed thereon that is also a helical thread. As with the internal thread 14 of the lumen 20, the external thread 26 may be right-handed or left-handed. Regardless of the handedness of the threads, the internal and the external threads 14, 26 may have a major diameter between about 9 mm and about 13 mm with a preferred range being between about 10 mm and about 12 mm. The major diameter tapers along a length of the insert at a ratio of the major diameter at the proximal end to the major diameter at the distal end in a range of about 1 to 2 with a preferred range of about 1.4 to about 1.7. Additionally, an angle of the taper may vary from about 10 degrees to about 60 degrees with a preferred angle ranging from about 18 degrees to about 56 degrees. It is envisioned that the internal thread 14 may be the same as the external thread 26 or they may differ in diameter, angle of taper, major diameter ratio, etc. It is contemplated that the internal thread 14 and the external thread 26 may differ in that one is a right-handed thread while the other is a left-handed thread. In one embodiment, the tapered portion of the external thread 26 extends along at least one-half of the length of the insert 20 and in a preferred embodiment, the tapered portion extends less than one-quarter of the length of the insert 20.

Figure 3A:
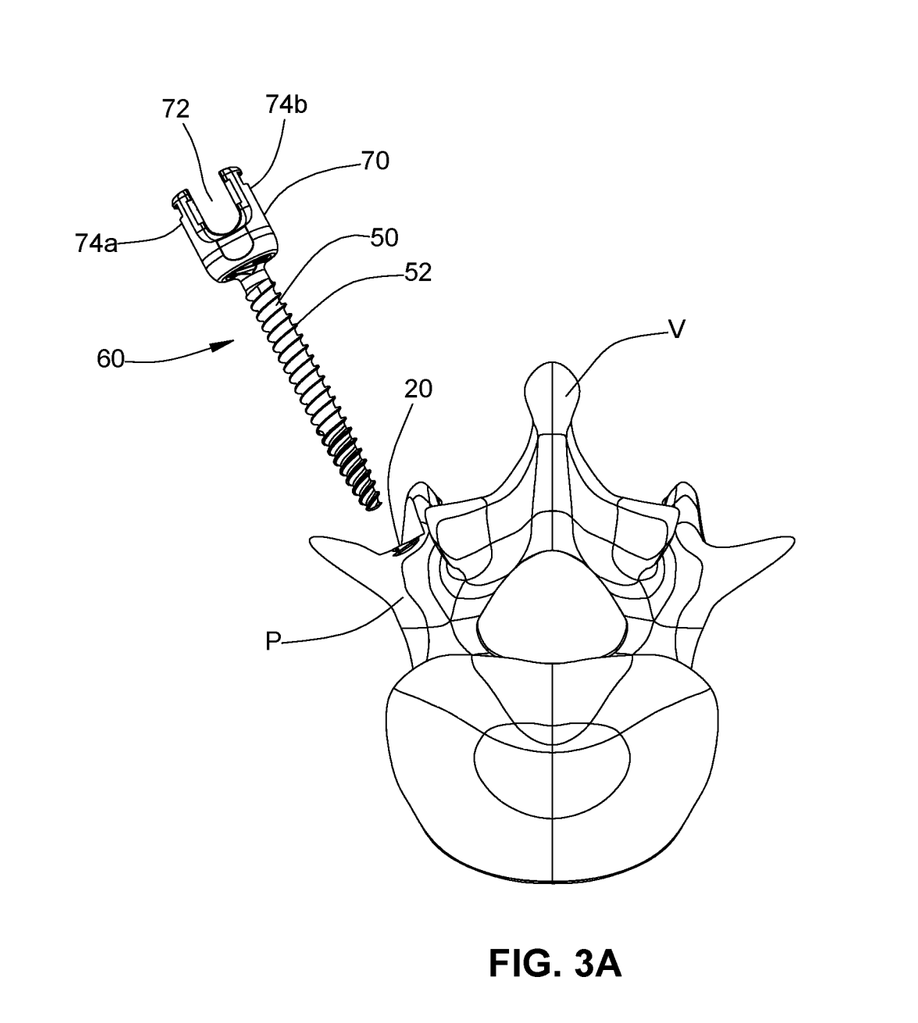
FIG. 3A is a perspective view of the insert of FIG. 1A positioned in the vertebra and a polyaxial pedicle screw.

The external thread 26 of the insert 20 is configured to cut into or engage with osseous tissue (i.e., bone tissue) while the internal thread 14 of the insert 20 is configured to engage with a thread of a bone screw 60 (FIG. 3C) as will be described in further detail hereinbelow. The insert 20 is particularly adapted for securement in cortical bone tissue. The insert 20 can be used to fill the geometry above the isthmus of a pedicle P (FIG. 3A) of a vertebra V (FIG. 3A). The insert 20 can fit within or stay above the isthmus of the pedicle P. This provides improved toggling strength over a conventional screw used alone because insert 20 is engaged with more bone tissue above the pedicle P. In particular, the insert 20 has a greater surface area than a bone screw (e.g., bone screw 60 of FIG. 3C) and this provides improved engagement between the insert 20 and bone tissue which, in turn, provides improved securement of the insert 20 in bone and reduces the possibility of the insert 20 being pulled out of bone.

The insert 20 may be used in situations where a hole or an opening exists in bone (e.g., a vertebra) with a diameter too large for a bone screw. This may result from a previous bone anchor installation and removal where the opening now has a diameter unsuitable for securing a bone screw therein or the opening has an incorrect orientation for proper securement of a bone screw. In such situations, the opening is resized to a diameter less than an outer diameter of the external thread 26 of the insert 20. Alternatively, an insert with a more suitable diameter for the existing opening is selected. The opening may be prepared using standard instruments such as a burr and then an awl to start the hole. A drill may be used to form the opening. Once the opening has been resized to accommodate the insert 20 or a suitable sized insert is selected for the opening, the insert 20 is driven into the opening as will be discussed hereinbelow. Alternatively, the insert 20 may be positioned in an opening prepared and dimensioned specifically for the insert 20. This opening is prepared using conventional tools (e.g., burr, awl, drill, etc.) and techniques. This may result from the target bone tissue having a relatively low density and using the insert 20 with its increased size relative to a bone screw provides improved securement as compared to using a bone screw by itself. Alternatively, the insert 20 is positioned in bone to increase the resistance to pull out in view of possible load values placed on the bone when the final spinal construct (e.g., screws and rod) is completed.

Figure 2B:
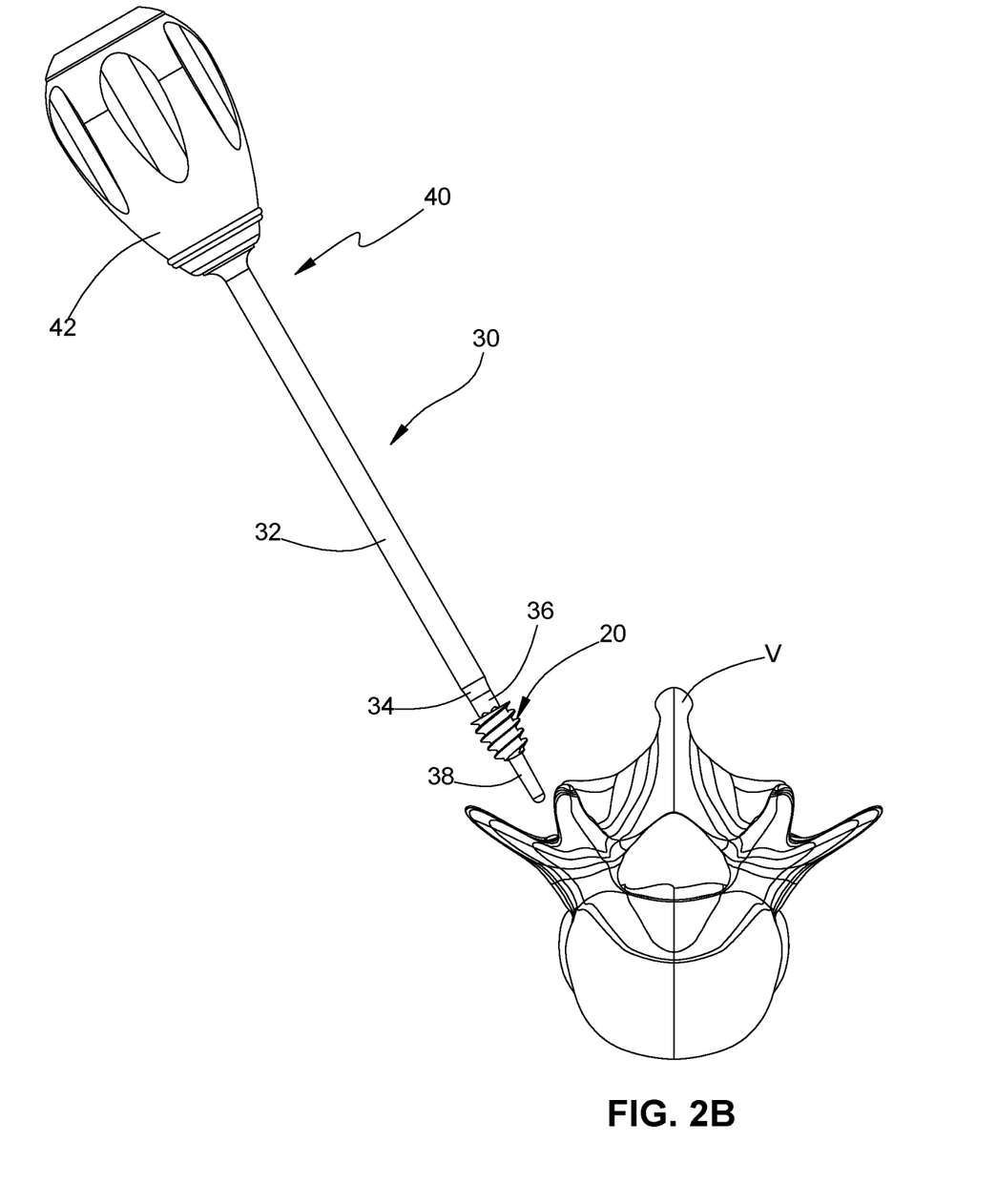
FIG. 2B is a perspective view of the insert of FIG. 1A coupled to the insertion instrument of FIG. 2A.
Figure 2C:
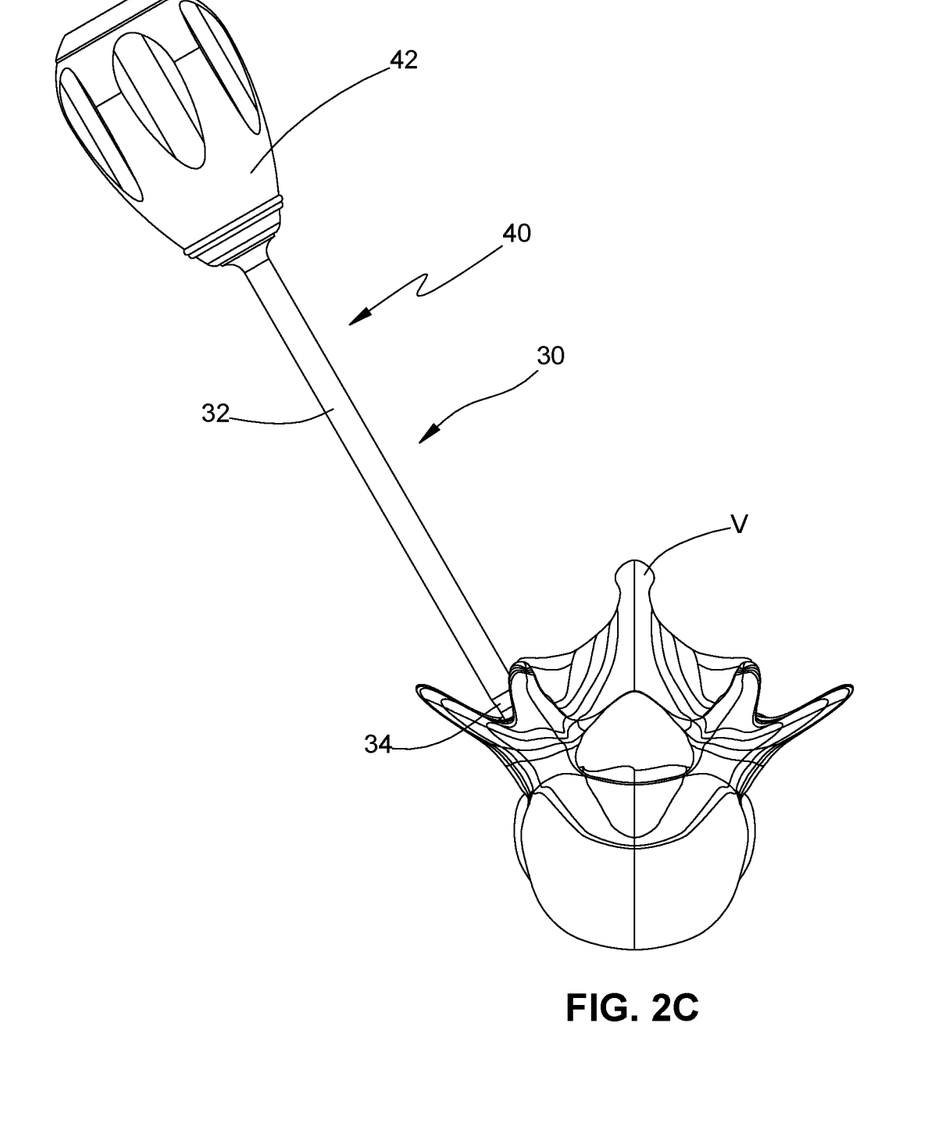
FIG. 2C is a perspective view of the insert of FIG. 1A positioned in the vertebra using the insertion instrument of FIG. 2A.

Once the target opening has been identified and/or prepared, the insert 20 is releasably coupled to an insertion instrument or insertion tool 40. As illustrated in FIGS. 2A-2C, the insertion tool 40 is an elongated instrument having a handle 42 at a proximal end thereof. The handle 42 may include ergonomic features such as alternating recesses as shown, knurling, or any other suitable finish allowing the clinician to have a more positive grip of the insertion tool 40. The insertion tool 40 has an elongate shaft 30 extending from the handle 42. The elongate shaft 30 has a first tubular portion 32 extending from the handle 42. A tapered collar 34 is located at the distal end of the first tubular portion 32. The collar 34 tapers in a proximal to distal direction. A second tubular portion 36 extends distally from the collar 34. The second tubular portion 36 has an outer diameter that is less than the outer diameter of the first tubular portion 32, but is substantially identical to an outside diameter of the distal end of the tapered collar 34. The second tubular portion 36 has a shoulder portion 36a with a geometric configuration that is complementary to the geometric configuration of the engagement portion 12 of the lumen 10 of the insert 20. This allows secure and releasable coupling of the insert 20 with the insertion tool 40. A third tubular portion 38 extends distally from the distal region of the second tubular portion. The third tubular portion 38 has an outer diameter less than the outer diameter of the second tubular portion 36. This permits the third tubular portion 38 to be inserted through the lumen 10 of the insert 20 so that the shoulder portion 36a of the second tubular portion 36 engages the engagement portion 12 of the lumen 10 of the insert 20. Thus, once coupled together, rotation of the handle 42 of the insertion tool 40 results in concomitant rotation of the insert 20. This allows the clinician to insert and/or remove insert 20 from the opening in bone.

Figure 3B:
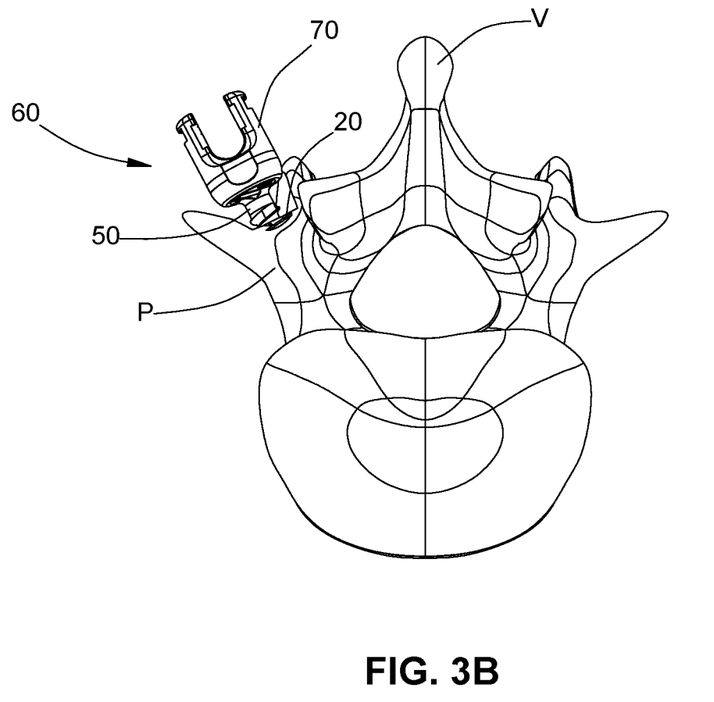
FIG. 3B is a perspective view of the insert of FIG. 1A positioned in the vertebra with the polyaxial pedicle screw of FIG. 3A coupled to the insert and defining a bone fixation apparatus.
Figure 3C:
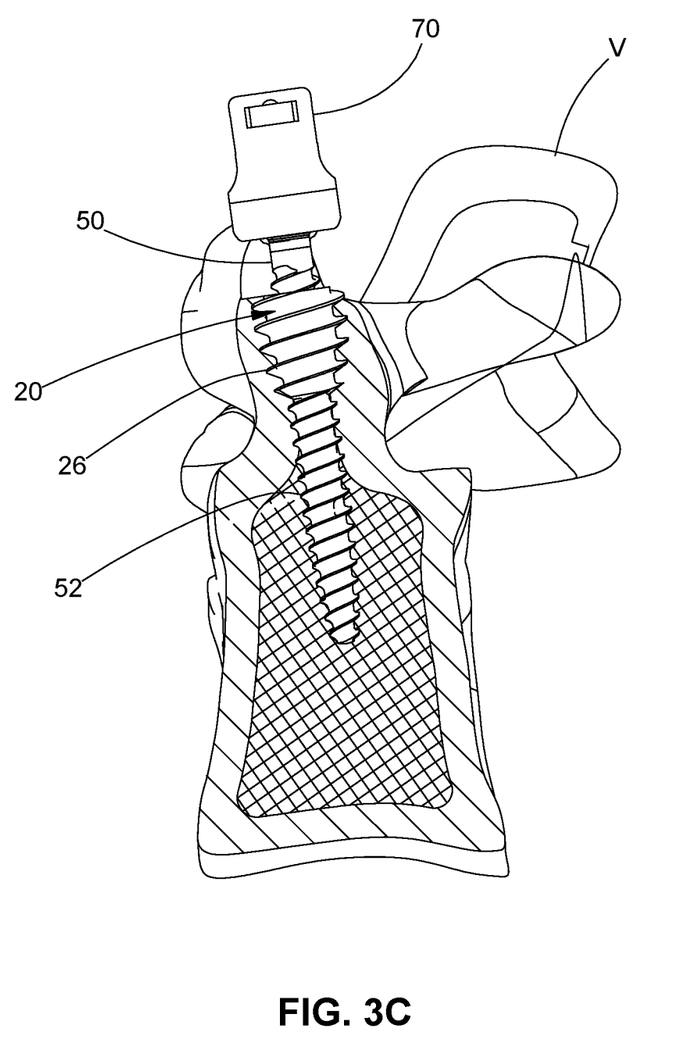
FIG. 3C is a partial cross-sectional view of the bone fixation apparatus of FIG. 3B disposed in the vertebra.

Referring now to FIGS. 3A-3C, with insert 20 properly positioned and secured in bone (i.e., a pedicle P of a vertebra V), a bone screw 60 is coupled to the insert 20 as follows. The bone screw 60 includes a shank 50 having a spherical head at one end that is received in a spherical recess in a housing 70. The housing 70 has a U-shaped channel 72 for receiving a spine rod (not shown). The U-shaped channel 72 is defined between two upstanding arms 74a, 74b that have internal threads for threadably engaging a setscrew (not shown). The shank 50 has a thread 52 disposed on an outer surface thereof. The thread 52 is a helical thread that is complementary to the internal thread 14 of the insert 20. Thus, if the internal thread 14 of the insert 20 is a right-handed thread, the thread 52 of the shank 50 is also a right-handed thread. The thread 52 of the shank 50 may have a major diameter between about 9 mm and about 13 mm with a preferred range being between about 10 mm and about 12 mm. The major diameter tapers along a length of the insert at a ratio of the major diameter at the proximal end to the major diameter at the distal end in a range of about 1 to 2 with a preferred range of about 1.4 to about 1.7. Additionally, an angle of the taper may vary from about 10 degrees to about 60 degrees with a preferred angle ranging from about 18 degrees to about 56 degrees. These sizes and relationships are selected to complement the configuration of the lumen 10 of the insert 20. Examples of suitable bone screws are disclosed in U.S. Pat. Nos. 8,814,919 and 9,393,049, the entire contents of which are hereby incorporated by reference herein.

A suitable driving tool or driver 200 (FIG. 5A) is coupled to the head of the shank 50 and a rotational force is applied to the driving tool 200 which causes concomitant rotation of the bone screw 60. Due to the complementary relationship between the thread 52 of the shank 50 and the internal thread 14 of the lumen 10, rotation in a first direction inserts the shank 50 of the bone screw 60 into the lumen 10 of the insert 20. It is contemplated that the length of the shank 50 may be less than the length of the insert 20 or it may be the same as the length of the insert 20 or it may be longer than the length of the insert 20 as illustrated in FIG. 3C. As the shank 50 of the bone screw 60 has a smaller outer diameter in comparison to the insert 20, the shank 50 of the bone screw 60 can be inserted through the insert 20 and into the isthmus of the pedicle P thereby reducing the risk of breaching the osseous tissue while at the same time providing sufficient pull out strength. Thus, a bone screw with a smaller diameter (e.g., 5.5 mm) can be used that would have pull out resistance comparable to a bone screw with a larger diameter (e.g., 6.5 mm).

The bone screw 60 may be modular such that the housing 70 may be replaced with a different housing or structure. By providing a modular arrangement, the clinician can modify the overall construct and tailor it to suit a particular procedure for a specific patient and that patient's anatomy. A different housing or other attachment structure allows for utilizing different sized rods, flexible tethers, plates, etc. to be part of the overall construct. An example of a suitable modular bone screw is disclosed in International Application No. PCT/US18/14179, filed on Jan. 18, 2018, the entire contents of which are incorporated herein by reference.

Figure 4:
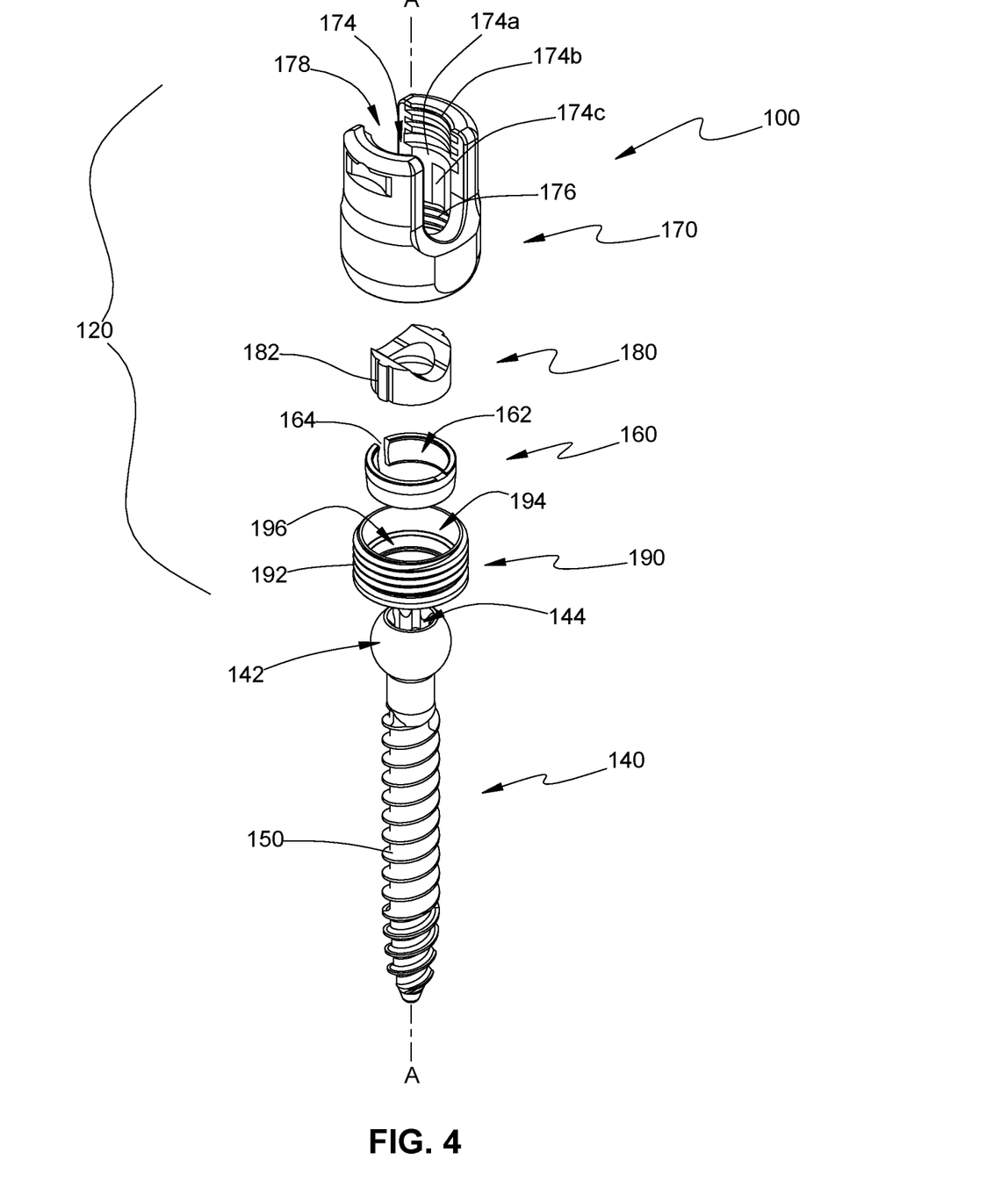
FIG. 4 is an exploded, perspective view, with parts separated, of a modular bone screw according to an embodiment of the present disclosure.
Figure 5A:
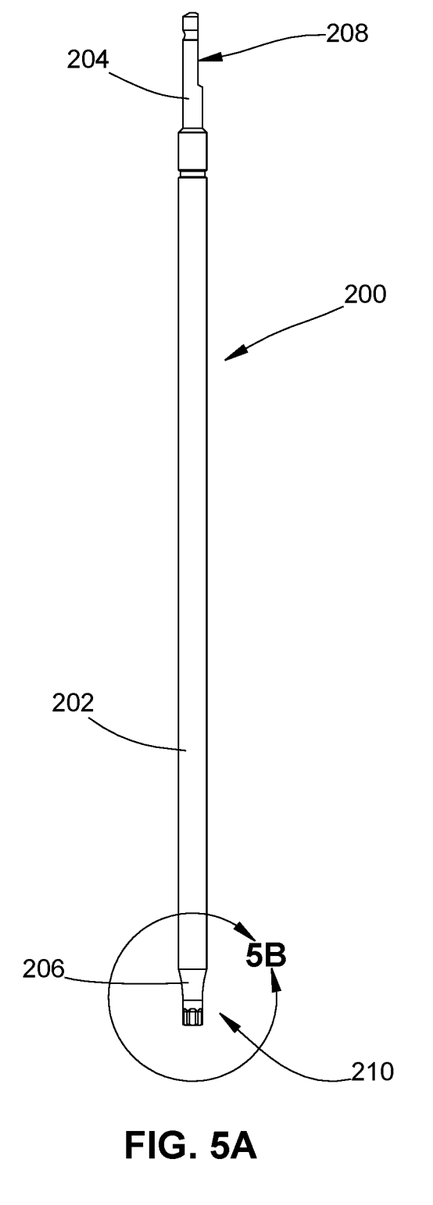
FIG. 5A is a plan view of a driving tool for rotating the bone screw of FIG. 3A.

Referring now to FIG. 4, another embodiment of a bone screw 100 is shown. The bone screw 100 includes a modular head assembly 120 and a screw member 140. The bone screw 140 includes a generally spherical head 142 at a proximal end thereof and a shank 150 extending distally therefrom. The head 142 of the bone screw 140 includes a tool engaging recess 144 that is configured to engage the engagement region 210 of the driver 200 (FIG. 5A). The bone screw 100 has a longitudinal axis A-A.

The modular head assembly 120 includes a housing 170, an anvil 180, a snap ring 160, and an insert 190. A through hole 174 extends through the housing 170. An inner surface 174a of a proximal portion of the through hole 174 includes threads 174b configured to threadably engage a setscrew (not shown). A distal portion of the inner surface 174a of the through hole 174 defines slots 174c disposed in juxtaposed relation to one another and extending along the longitudinal axis A-A. The slots 174c are configured to slidably engage tabs 182 of the anvil 180 to enable translation of the anvil 180 within the through hole 174, but inhibit rotation of the anvil 180 within the through hole 174. In this manner, the slots 174c ensure that a U-shaped slot 178 of the housing 170 remains aligned with a concave relief defined in the anvil 180. The U-shaped slot 178 is configured to receive a spinal rod (not shown). Additionally, the housing 170 includes inner threads 176 disposed in a distal region of the housing 170.

The snap ring 160 is configured to be slidably received within a portion of the insert 190. The snap ring 160 may be formed from a resilient material that enables the snap ring 160 to expand and contract without being permanently deformed. The snap ring 160 has a lumen 162 defined between upper and lower surfaces of the snap ring 160. An inner surface of the snap ring 160 defines a generally concave profile corresponding to the profile of the head 142 of the bone screw 140. An outer surface of the snap ring 160 defines a slot 164 that interrupts a perimeter of the snap ring 160 such that the snap ring 160 forms a generally C-shaped profile which enables the snap ring 160 to expand and contract due to an external or internal force being applied thereto.

With continued reference to FIG. 4, the insert 190 has a generally cylindrical profile extending between proximal and distal surfaces. An outer surface of the insert 190 defines threads 192 configured for threadably engaging the inner threads 176 of the housing 170 such that the insert 190 is threadably coupled to the housing 170. The insert 190 includes a first counterbore 194 and a second counterbore 196. The second counterbore 196 is concentric with the first counterbore 194 and has a diameter that is less than the diameter of the first counterbore 194. In this manner, the first counterbore 194 is configured for slidably receiving the snap ring 160 therein whereas the second counterbore 196 is configured to compress the snap ring 160 as the snap ring 160 is received therein. In this manner, the second counterbore 196 compresses around the head 142 of the bone screw 140 to secure the bone screw 140 in position relative to the housing 170. The inside diameter of the insert 190 is configured and dimensioned such that the head 142 of the bone screw 140 is capable of passing through the insert 190.

Figure 5B:
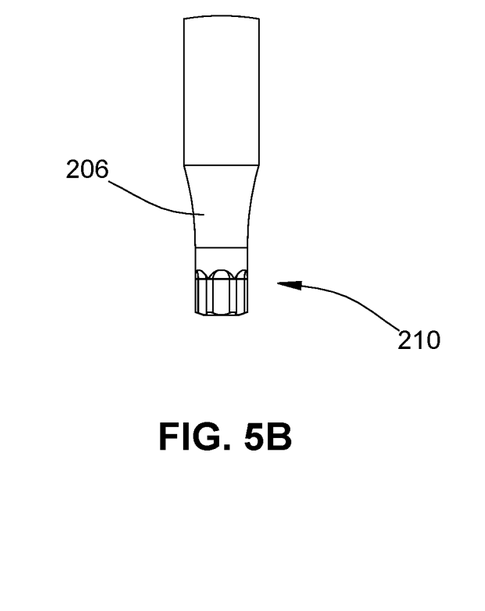
FIG. 5B is an enlarged view of the area of detail in FIG. 5A.

With reference to FIGS. 5A and 5B, a driving tool or driver suitable for use with either bone screw 60 or bone screw 100 is provided and generally identified by reference numeral 200. The driver 200 includes an elongate shaft 202 having a proximal portion 204 and an opposed distal portion 206. The proximal portion 204 of elongated shaft 202 defines a handle attachment feature 208 that is configured to apply a driver handle (not shown) to enable selective application of rotational force to driver 200 (e.g., a clinician grips handle (not shown) and applies rotational force thereto). The distal portion 206 of the driver 200 tapers to a driving, but reduced diameter engagement region 210. The engagement region 210 includes protrusions and recesses that are complementary to the tool engaging recess 144 of the bone screw 140 or the tool engaging recess (not shown) of bone screw 60. Once the engagement region 210 is inserted into the tool engaging recess 144, rotation of the driver 200 results in rotation of the bone screw 140. Thus, the driver 200 is capable of rotating the bone screw 140 for insertion or removal of the bone screw 100 into bone. It is envisioned that driver 200 may be used with a setscrew (not shown) for inserting and/or removing a setscrew from either housing 70 or housing 170.

It is contemplated that any of the above-described components may be formed from any biocompatible material suitable for use in surgical procedures, such as titanium, titanium alloys, (e.g., Ti-6Al-4V), stainless steels, cobalt chrome alloys.

It will be understood that various modifications may be made to the embodiments of the presently disclosed retraction system. Therefore, the above description should not be construed as limiting, but merely as exemplifications of embodiments. Those skilled in the art will envision other modifications within the scope and spirit of the present disclosure.

What is claimed is:

1. A bone fixation apparatus comprising:
    an insert having an open proximal end and an open distal end defining a lumen therethrough, the open proximal end having a geometric pattern for mating with a driving tool;
    a first helical thread disposed on an outer surface of the insert, the first helical thread configured to engage bone;
    a second helical thread disposed in the lumen of the insert, the second helical thread extending substantially from the open proximal end of the insert to the open distal end of the insert; and
    a bone anchor having a bone screw member and a housing, the bone screw member including a spherical head and a shank extending, therefrom, the shank having a third helical thread on an outer surface thereof, the spherical head movably retained in a cavity of the housing, the second helical thread engageable with the third helical thread such that the bone anchor is coupled to the insert.

2. The bone fixation apparatus of claim 1, wherein the second and third helical threads are reversed from the first helical thread.

3. The bone fixation apparatus of claim 1, wherein the open proximal end includes alternating lobes and recesses defining a hexolobular geometric configuration.

4. The bone fixation apparatus of claim 1, wherein the first helical thread is configured to engage osseous tissue in a pedicle of a vertebra.

5. The bone fixation apparatus of claim 1, Wherein the lumen of the insert slidably receives a portion of the driving tool.

6. The bone fixation apparatus of claim 1, wherein a major diameter of the first helical thread is between about 10 mm and about 12 mm.

7. The bone fixation apparatus of claim 6, wherein the major diameter of the first helical thread tapers along a length of the insert.

8. The bone fixation apparatus of claim 7, wherein the major diameter tapers from a proximal end of the insert towards the distal end of the insert at a ratio of about 1.4 to about 1.7.

9. The bone fixation apparatus of claim 7, wherein an angle of the taper is between about 18 degrees and about 56 degrees.

10. A method of inserting a bone fixation apparatus comprising:
    attaching a non-expandable insert to a driving tool;
    positioning a distal portion of the driving tool proximate a target location on bone such that the insert is proximate the target location;
    securing the insert in bone by rotating the driving tool such that a first thread of the insert rotatably engages bone;
    removing the driving tool from the insert; and
    coupling a bone anchor to the insert, the bone anchor including a housing and a screw member, the screw member having a threaded shank engageable with a second thread in a lumen of the insert.

11. The method of inserting the bone fixation apparatus of claim 10, further including creating an opening in the vertebra at the target location.

12. The method of inserting the bone fixation apparatus of claim 10, further including preparing a preexisting opening at the target location to receive the insert therein.

13. The method of inserting the bone fixation apparatus of claim 11, wherein creating the opening includes the opening positioned on a pedicle of the vertebra.

14. The method of inserting the bone fixation apparatus of claim 12, wherein preparing the preexisting opening includes the preexisting opening disposed on a pedicle of the vertebra.

15. The method of inserting the bone fixation apparatus of claim 10, wherein coupling the hone anchor to the insert includes the hone anchor having a modular housing.

* * * * *